United States Patent
Lin et al.

(10) Patent No.: US 6,491,688 B1
(45) Date of Patent: Dec. 10, 2002

(54) APPARATUS AND METHODS FOR REVERSAL OF PRESBYOPIA USING NEAR INFRARED SELECTIVE LASER ON ZONNULAS

(76) Inventors: J. T. Lin, 4532 Old Carriage Trail, Oviedo, FL (US) 32765; Heraldo Sa Martins, Rua Jose Osorio 359 - Madalena, Recife PE 50610 (BR)

( * ) Notice: Subject to any disclaimer, the term of this patent is extended or adjusted under 35 U.S.C. 154(b) by 0 days.

(21) Appl. No.: 09/598,518

(22) Filed: Jun. 21, 2000

(51) Int. Cl.$^7$ ............................................... A61B 18/18
(52) U.S. Cl. ................................... 606/6; 606/4; 606/5
(58) Field of Search ........................................ 606/2–19

(56) References Cited

U.S. PATENT DOCUMENTS

| | | | | |
|---|---|---|---|---|
| 3,943,931 A | * | 3/1976 | Krasnov | 606/17 |
| 5,152,760 A | * | 10/1992 | Latina | 606/6 |
| 5,290,272 A | * | 3/1994 | Burstein et al. | 606/4 |
| 5,376,086 A | * | 12/1994 | Khoobehi et al. | 606/4 |
| 5,529,076 A | * | 6/1996 | Schachar | 128/898 |
| 5,548,352 A | * | 8/1996 | Dewey | 351/160 H |
| 6,033,396 A | * | 3/2000 | Huang et al. | 606/5 |

* cited by examiner

*Primary Examiner*—Michael Peffley
*Assistant Examiner*—Peter J Vrettakos

(57) ABSTRACT

A method and apparatus for presbyopia correction are disclosed. The disclosed preferred embodiments of the system consists of a beam spot controller, a beam delivery device, a slit lamp, a visible aiming beam and a selected solid state laser having a wavelength of (0.9–1.4) microns. Presbyopia is treated by the thermal contraction of the human zonnulas with a temperature increase of about (15–50) degree-C generated by the selected lasers. The near infrared laser is focused and delivered by a gonio lens to the target zonnulas area and viewed by a surgeon using a slip lamp. The selected laser having an optimal absorption characteristics is tightly focused such that only the target zonnulas is heated, while the cornea, the lens body and the adjacent areas are not damaged.

6 Claims, 4 Drawing Sheets

APPARATUS AND METHODS FOR REVERSAL OF PRESBYOPIA USING NEAR INFRARED SELECTIVE LASER ON ZONNULAS

BACKGROUND OF THE INVENTION

1. Field of the Invention

The present invention relates to method and apparatus for effecting controlled thermal contraction or shrinkage of zonnular tissue fibers to provide a non-invasive reversal of presbyopia, by means of a selective laser which is focused and delivered by a special device.

2. Brief Description of the Prior Art

Presbyopia has been a challenging disease for medicine. Eye glasses and contact lens are the most common method of compensating for presbyopia. Multifocal intraocular lens also have been employed but restricted to cataract patients. These procedures merely compensate for presbyopia, instead of restoring accommodation. Therefore, the suitable procedures for presbyopia patients to be cured are limited to those methods which involve reversal of presbyopia by acting upon the area of lens, zonnulas, ciliary body, and sclera. Reshaping the cornea with an excimer laser to form bifocal shape produces glare, halos and unacceptable monocular diplopia.

Procedures for presbyopic correction using insertion of rigid bands were proposed by R. A. Schachar in U.S. Pat. Nos. 5,529,076, 5,489,299 and 5,722,952. In the prior arts of Schachar a multitude of claims were made, being the great majority restricted to abstractions. Specially in U.S. Pat. No. 5,503,165 it claims to cover all lasers from the electromagnetic spectrum for contracting the zonnulas and reversing presbyopia. Contracting the zonnulas to reverse presbyopia is a tangible medical method. However the zonnulas are deprived of pigment and therefore can not be heated by many of the lasers cited by Schachar's prior arts.

It is further believed that Schachar had incorrectly assumed that all lasers will act on pigment-free tissues such as the zonnulas. Many of the lasers cited by the prior arts of Schachar are photoablative and simply would not cause thermal effects on the zonnulas. Furthermore, in these prior arts, there was no mention of any specific laser parameters which is capable of causing the thermal shrinkage of the zonnulas and only abstract idea was suggested which covered all existing lasers. On the other hand, one of the present inventors (Martins), filed a U.S. patent application called "Laserthermozonnuloplasty" on Jan. 23, 1997, U.S. appl. Ser. No. 08/792,848, describing the idea of laser presbyopia reversal. This patent was abandoned later by the present author in virtue of the fact that, just as Schachar's, it was only an abstraction and lack of specific laser parameters and the focusing means to restrict the laser thermal energy to the target tissue (zonnulas). Without specifying the laser parameters and its delivery means, the abstraction suggested by the prior arts will not provide a clinically useful system. Furthermore, non of the idea suggested by the prior arts has been tested by a device.

One of the present inventors (Lin) also proposed the use of lasers for presbyopic corrections by removal of a portion of the scleral tissue over the ciliary body, U.S. patent application Ser. Nos. 09/189,609 and 09/303,673. These methods, however, are invasive and laser ablation depth is critical for the clinical outcome and safety.

It is one of the objects of the present invention to provide a laser system which offers a non-invasive method and apparatus to correct presbyopia. Our present invention came from the expertise of one of the inventors in ophthalmology (Martins) and the knowledge of the other in laser physics (Lin). It is specific in the mode and applicable principles. It describes the manner and process of making and using a laser and related accessories in order to achieve zonnular contraction, concisely and exactly. The proposed method shall apply to out-patients and involves no implanting, no tissue cutting or ablating, no suturing, no bleeding and can be performed easily and fast.

It is yet another object of the present invention to provide the details of a mean to deliver the laser to the targeted-area without significant damage to the other surrounding tissues. Specific laser spot size, beam focusing and tissue absorption are critical in the proposed method for safety and clinical outcomes. The desire is to heat selected areas of rich in collagen tissue to a shrinkage level, but without damage or destruction of either the target or surrounding tissues. In other words, the selective laser is used to irradiate the zonnulas tissue with energy such that the temperature of the collagen tissue is raised sufficiently to cause the tissue to shrink but not so high as to cause any substantial damage. The thermal shrinkage of the selected zonnulas area of the eye will cause the zonnulas to change its shape, decreasing its length, and then reverse presbyopia.

It is yet another object of the present invention to provide a laser system which is portable, compact and easy to be integrated with a slip lamp.

Other than these above mentioned, no other author of our knowledge had ever proposed or designed a device for contracting the zonnulas for correcting presbyopia or presented anything beyond mere abstractions. To our knowledge we are the first ones to propose a practical medical device for successfully contract the human zonnulas.

SUMMARY OF THE INVENTION

The system proposed in the present invention consists of an infrared laser which is focused to the human zonnulas, where it will provoke a thermal contraction. It is attached to a slit lamp and shot through an ophthalmic gonio lens, aimed at the equatorial zonnulas and aided by a visible aiming laser that assists in focusing in the precise location. The laser has the characteristic of partial water absorption, not needing a chromophore (pigment) in order to produce a localized increase in temperature at the laser focal point. The increase in temperature in the beam pathway, due to partial water absorption, is far less than that obtained at the focal point due to the cone shape of the beam, which favors dissipation. In the present invention, the desire is to heat selected areas of rich in collagen tissue to shrinkage levels, but without damage or destruction of either the target or surrounding tissues. The thermal shrinkage of the selected zonnulas area of the eye will cause the zonnulas to change its shape, decreasing its lengths and reverse presbyopia. For the first time in medicine this process is being used and will be useful not only for correction of presbyopia but also any ophthalmic disease that requires focal heat in tissues with high water and protein content.

To achieve the proposed selected thermal shrinkage of the zonnulas and increase the accommodation of presbyopia patient, the system design must meet the following requirements: (1) the absorption of the laser beam in its propagation path inside the eye is optimal, not too high to cause damage other than the selected area to be shrinkaged, but high enough to cause the thermal effect on the selected area; (2) the laser beam shall be focused and enter the eye in a cone shape having the focal point near the selected target; and (3) the thermal shrinkage of the selected area shall cause the lens to change its shape such that the patient's eye can accommodate to see both far and near. The zonnulas are considered to be relatively inert in its steady state, and while thermally induced contraction occurs by the process of this invention, temperatures are bellow the thermal traumatic or inflammatory thresholds. In absence of trauma, the dimensional collagen reconfiguration is believed to exhibit long-term stability.

DETAILED DESCRIPTION OF THE PREFERRED EMBODIMENT

This invention is directed to tissue shrinkage by the use of a laser coherent energy in the near infrared wavelength range of about (0.9–1.3) microns, and preferably in the range of about (0.96–1.0) microns, as generated by diode lasers. This type of diode laser is relatively compact and easy to operate, and is capable of generating energy optimally absorbed within the selected area of the eye based on the spectral-absorption coefficients of these wavelengths (about 0.2 to 1.0 reverse cm), without damage or destruction of adjacent tissue. The thermal shrinkage of the selected area of the eye will cause the zonnulas to change its shape, decreasing its length, and reverse presbyopia.

Figure 1:
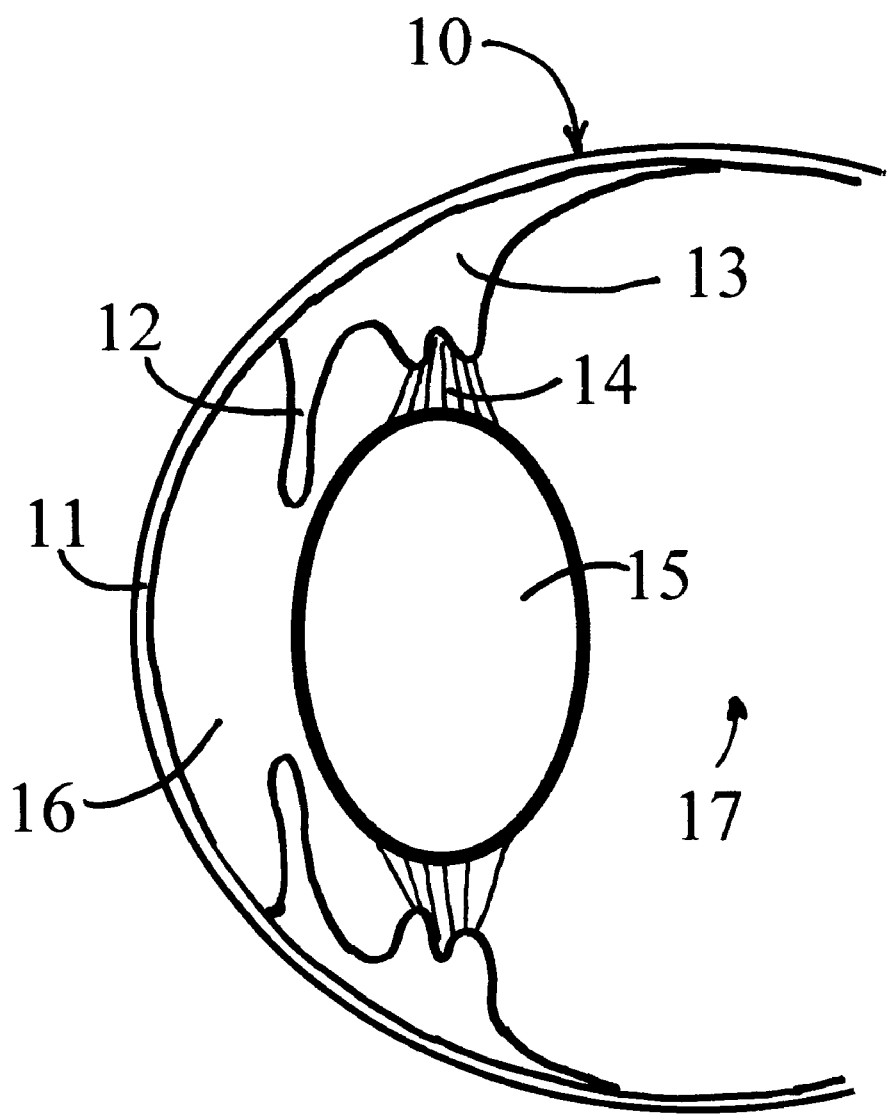
FIG. 1 is a horizontal sectional view of an eye.

To define the selected areas of the eye to be treated by a laser, we show, in FIG. 1, a horizontal section of an eye 10 having roughly a spherical and transparent cornea 11 at the central portion. The eye's iris 12 is positioned between the cornea 11 and lens 15 to divide the space forward of the lens into an anterior chamber 16 and posterior chamber 17 filled with watery aqueous humor. The crystalline lens 15 is supported by zonnular ligaments 14 and connected to the ciliary body 13. The zonnular ligaments and the ciliary body muscle regulates the thickness (shape) of the lens by accommodation and enable the eye to focus on objects at various ranges. The space behind the lens is filled with a clear gel-like body 17 called vitreous humor. In the patent pending inventions of J. T. Lin, application Ser. Nos. 09/189,609 and 09/303,673, it was proposed to use non-thermal lasers to remove a portion of the scleral tissue over the ciliary body 13 to increase the accommodation of a presbyopic patients. In the present invention, we propose thermal lasers to selectively deliver its thermal energy at the zonnulas area 14.

Figure 2A:
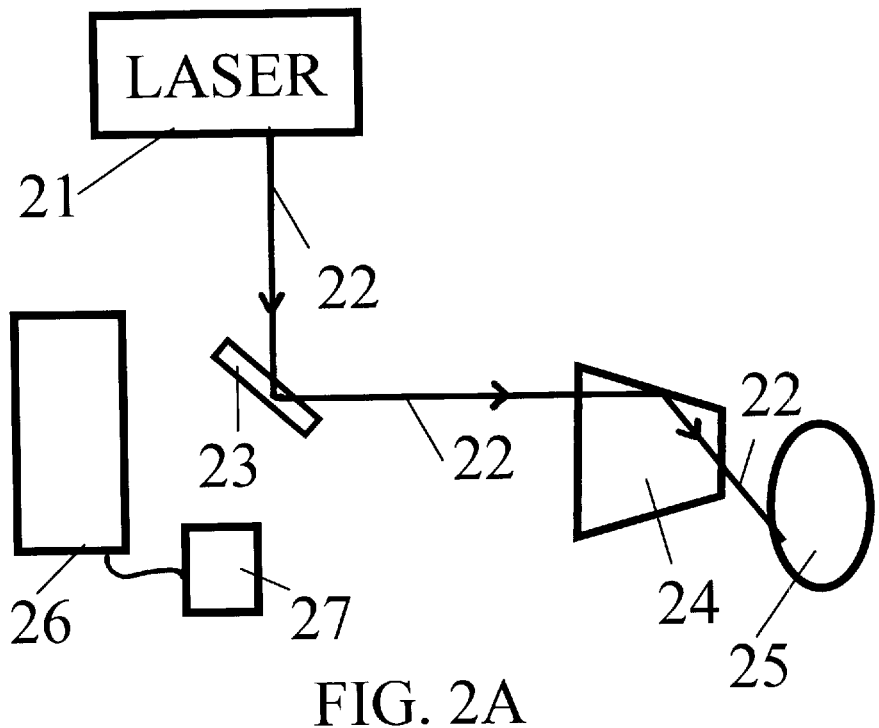
FIG. 2 is a block diagram of the apparatus of the invention, where (A) shows the overall structure and surgeon's view and (B) shows the beam path inside the gonio lens.
Figure 2B:
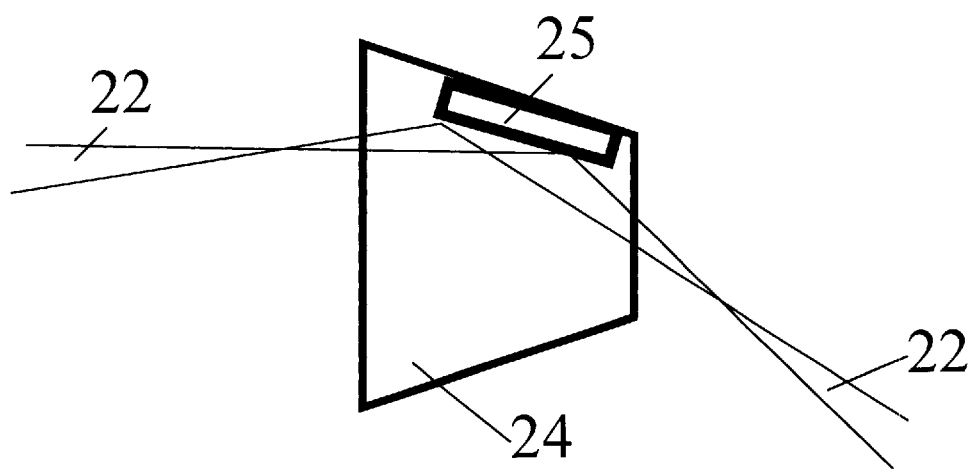

In the present invention, the desire is to heat selected areas specially rich in collagen tissue to a shrinkage level, but without damage or destruction of either the target or surrounding tissues. Preferably, the optical-delivery-system laser is integrated with a slip lamp to enable the surgeon to define the target area. As shown in FIG. 2A, the system consists of a laser system 21 having a wavelength 22 and reflected by a mirror 23 and coupled by a gonio lens 24 to the patient's eye 25. Patient's eye and the laser beam path is viewed by a surgeon through a slip lamp 26. The laser system is computer controlled for laser energy or power level and the illuminating time triggered by a footswitch 27. FIG. 2B shows the detail of a gonio lens 24 having a reflection mirror 25 to deliver the focused laser beam 22 to the selected target area at a predefined spot size and energy level. A commercially available gonio lens will typically have three pieces of reflecting mirrors at different angles. In addition, the laser may be delivered to the targeted area in a circular pattern, at the lens equator area, by rotating the gonio lens.

Figure 3:
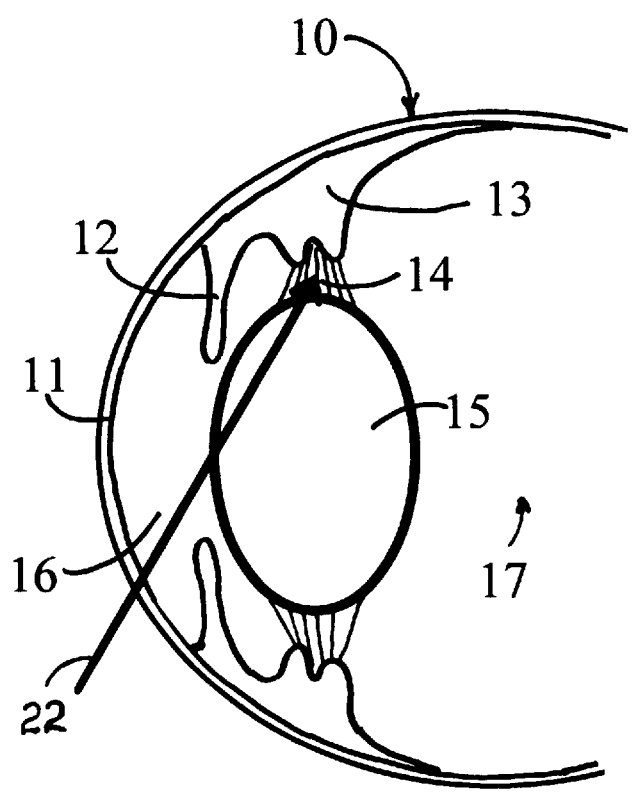
FIG. 3 is a horizontal sectional view of an eye and the laser treated area of zonnular ligaments.

FIG. 3 shows the position of the focused laser at targeted area by selection of the reflecting gonio lens angle. The preferred gonio angle varies with eye anatomy and primary position of the mirror. A wide papillary dilation is mandatory for perfect visualization and treatment of the zonnulas. The proposed gonio lens angle is about (50–70) degrees in order to reach the zonnulas area.

The research underlying this invention includes experiments with pig's eyes, propagation of a focused infrared diode laser in water and laser beam reflected by a gonio lens to a target tissue. The significant feature is that desired peak temperatures are confined to the selected area of the zonnular ligaments such that corneal tissue, anterior chamber and ciliary body will not be damaged by the coneshape focused laser which has a larger spot size or much lower fluency in these non-target areas. Lens equator may receive heat enough to form a punctiform cataract that does not affect vision. This cataract formation may be caused by insufficient pupilary dilation.

Figure 4:
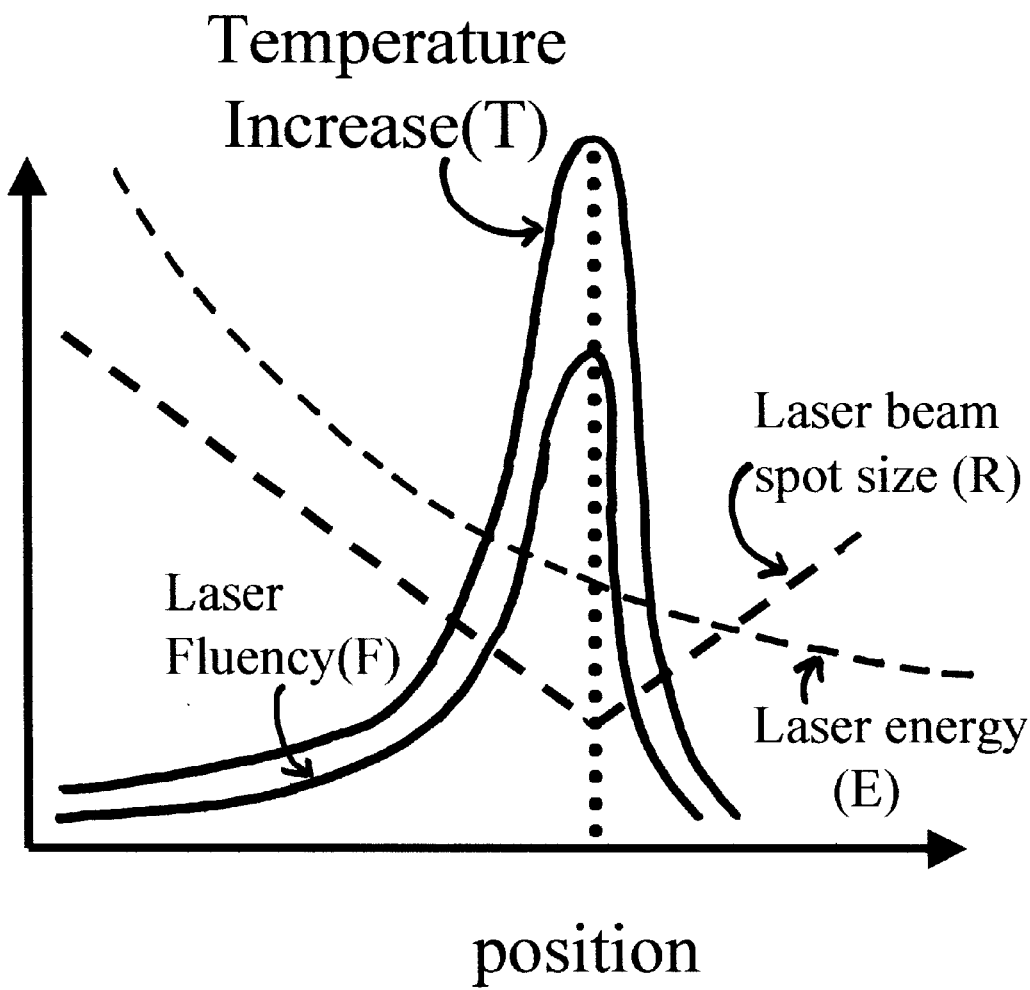
FIG. 4 shows laser parameters and the temperature increase versus laser beam position in the eye.

The proposed selective laser effect requires the laser beam to enter the eye in a coneshape with an angle large enough to localize the laser fluency at the target area. FIG. 4 shows the schematic of the concept requirement for laser fluency (F), laser beam spot diameter (R), laser energy (E) and the temperature increase (T) of the eye at various position of the laser beam path. By focusing the laser beam at the target area (shown by dotted vertical line), we expect the laser spot size (R) is minimum at the focal point and hence the fluency (F) and the temperature increase (T) have a peak value at the target area. The laser energy (E) is exponentially decreased according to Beer's law. However, the absorption of the beam path prior to the target area can not be too high, typically less than about 50%, in order to achieve enough temperature increase at the target area while keeping the adjacent tissues unheated or minimum heated. The curves of FIG. 4 are theoretically predicted by the following relationships among these parameters: F is proportional to the square of R; T is proportional to F and laser absorption coefficient; E is inverse proportional to the exponential of R. Therefore when the laser beam is focused into a weakly absorbing medium we shall expect the "narrow" peak of temperature increase (T) at the focused target area which in turn avoids the damage of other non-focused areas.

Figure 5:
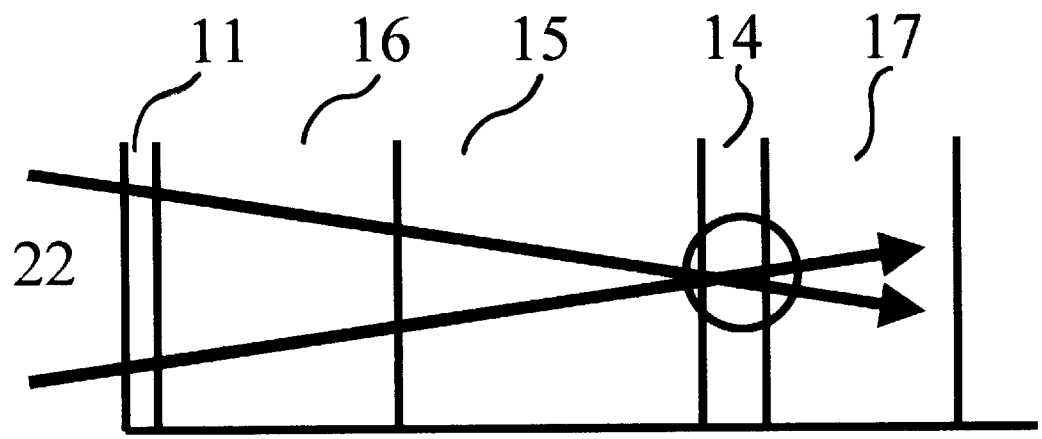
FIG. 5 is a schematic cross-sectional view of propagation of the laser in the eye with focused area in zonnular ligaments.

FIG. 5 shows the focused laser beam 22 propagating in the eye with the targeted area indicated by a circle, where the target area 14 is the zonnulas. This figure shall be compared to FIG. 3 for a more clear view of the eye position and the laser beam path. It is critical that the laser beam 22 will not cause thermal damage at the non-focused areas including the cornea 11, the anterior chamber 16, the lens body 15, and the posterior chamber 17.

The laser application patterns at the target area of zonnulas may be achieved by rotating the gonio lens. The treatment method is not limited to application of shrinking heating in pattern of circular dots and in circle ring. It is also optically possible to apply the shrinkage energy as a narrow line, or as a pattern of lines forming a rectangle or other shapes. Depending on the selected energy pattern and the spot size, the applied average power per "shot" is typically in the range of about (0.5–2.0) watts.

One of the key objectives of this invention is to achieve a shrinkage-producing temperature elevation of at about (15–50) degree-C in the target area while preventing destructive temperature increases in the adjacent areas. This goal is achieved by use of the recommended coherent wavelengths (and associated absorption coefficients) at moderate average power of about (0.5–2.0) watts on the zonnulas. The selective laser may be operated in a burst or pulse mode, or gated c-w mode with a width in the range of (0.1–2.0) seconds.

It is also within the scope of this invention to apply multiple shots of temperature-elevating energy to each tissue zone in which shrinkage is to be effected. For example, two or three energy pulses (each of about 10–50 milliseconds duration) may be applied to a single zone, with short-duration interpulse separation of about (100–500) milliseconds.

While the invention has been shown and described with reference to the preferred embodiments thereof, it will be understood by those skilled in the art that the foregoing and other changes and variations in form and detail may be made therein without departing from the spirit, scope and teaching to the invention. Accordingly, threshold and apparatus, the ophthalmic applications herein disclosed are to be considered merely as illustrative and the invention is to be limited only as set forth in the claims.

We claim:

1. A method of correcting presbyopia by thermal contracting the zonules of a human eyeball, said method comprising the steps of:

(a) selecting a laser having all output beam of predetermined infrared wavelength;

(b) selecting a gonio lens which is rotated to generate the desired thermal patterns of the said selected laser on the zonules.

2. A method of claim 1, in which the said selected laser is a solid state laser having an output wavelength of about (0.9–1.4) microns and average power of about (0.2–2.0) watts on the zonules.

3. A method of claim 1, in which the said selected laser is a diode laser having an output wavelength of about (0.9–1.4) microns and average power of about (0.2–2.0) watts on the zonuls.

4. A method of claim 1, in which the zonules tissue is heated by the said selected laser with a temperature increase of about (15–50) degree-C.

5. A method of claim 1, in which thermal pattern on the zonules is circular dots.

6. A method of claim 1, in which the thermal pattern on the zonules is circular rings.

* * * * *